United States Patent
Treacy (12)

(10) Patent No.: US 6,209,621 B1
(45) Date of Patent: *Apr. 3, 2001

(54) IMPLANTABLE PROSTHESES WITH METALLIC POROUS BEAD PREFORMS APPLIED DURING CASTING AND METHOD OF FORMING THE SAME

(75) Inventor: Debra J. Treacy, Middleborough, MA (US)

(73) Assignee: Depuy Orthopaedics, Inc., Warsaw, IN (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/499,743

(22) Filed: Jul. 7, 1995

(51) Int. Cl.[7] ............................ B22C 9/02; B22C 9/00; B22D 19/14
(52) U.S. Cl. ........................ 164/516; 164/35; 164/97
(58) Field of Search ...................... 29/527.5; 164/9, 164/10, 34, 35, 45, 97, 98, 516

(56) References Cited

U.S. PATENT DOCUMENTS

| | | | |
|---|---|---|---|
| 1,953,075 | * 4/1934 | Collins | 164/9 X |
| 3,855,638 | 12/1974 | Pilliar | 3/1 |
| 4,355,428 | 10/1982 | Deloison et al. | 3/1.91 |
| 4,600,546 | 7/1986 | Grundei | 264/59 |
| 4,608,052 | 8/1986 | Van Kampen et al. | 623/22 |
| 4,612,160 | 9/1986 | Donlevy et al. | 419/2 |
| 4,722,870 | 2/1988 | White | 428/621 |
| 4,781,721 | 11/1988 | Grundei | 623/16 |
| 4,854,496 | * 8/1989 | Bugle . | |
| 5,004,034 | * 4/1991 | Park et al. . | |
| 5,010,945 | * 4/1991 | Burke . | |
| 5,016,702 | 5/1991 | Ahlers | 164/34 |
| 5,027,998 | 7/1991 | Bugle | 228/44.5 |
| 5,042,560 | 8/1991 | Ahlers | 164/34 |
| 5,108,435 | 4/1992 | Gustavson et al. | 623/16 |
| 5,178,201 | 1/1993 | Ahlers | 623/22 |
| 5,192,324 | 3/1993 | Kenna | 623/16 |
| 5,201,766 | 4/1993 | Georgette | 623/16 |
| 5,236,457 | * 8/1993 | Devanathan . | |
| 5,246,530 | 9/1993 | Bugle et al. | 156/643 |
| 5,297,609 | * 3/1994 | Cook . | |
| 5,433,440 | * 7/1995 | Lin | 29/527.5 X |
| 5,441,537 | 8/1995 | Kenna | 419/2 |
| 5,535,810 | 7/1996 | Compton et al. | 164/35 |
| 5,687,788 | * 11/1997 | Caldarise et al. . | |
| 5,713,410 | * 2/1998 | LaSalle et al. . | |

* cited by examiner

Primary Examiner—S. Thomas Hughes
Assistant Examiner—Marc Jimenez
(74) Attorney, Agent, or Firm—Nutter, McClennen & Fish, LLP

(57) ABSTRACT

An implantable prosthesis having porous textured surface regions and methods for making the same provide improved prostheses and prosthesis manufacturing methods. The implantable prostheses contain one more bead preforms that are secured to the metallic prosthesis components during the casting process to form porous textured surface regions in desired areas of the prostheses.

16 Claims, 3 Drawing Sheets

IMPLANTABLE PROSTHESES WITH METALLIC POROUS BEAD PREFORMS APPLIED DURING CASTING AND METHOD OF FORMING THE SAME

BACKGROUND OF THE INVENTION

The invention relates to implantable prostheses and methods for forming the same. More particularly, the invention relates to implantable prostheses having metallic porous textured surfaces applied during casting, and casting methods for forming the same.

Implantable bone prostheses are often made by an investment casting process. Investment casting first requires the manufacture of a solid model of the article to be cast. The solid model can be made from a meltable wax or from other heat disposable materials by several known techniques. Once the solid model is made, one or more of the solid models are fixed to a riser, such as a wax tree, and the entire assembly is then encased in a refractory binder material. This done by successive treatments of the assembly with a ceramic slurry coating, following by drying the coating between treatments. After final drying, the resulting investment assembly is heated to a temperature sufficient to melt and extract the casting wax or other heat disposable material from within the shell. Thereafter, the shell may be sintered or fired at a higher temperature to strengthen the shell and to burn off any residue. Molten metal is then poured into the investment assembly to fill the cavities once occupied by the solid models.

An important consideration in the design and manufacture of virtually any implantable bone prosthesis is that the prosthesis have adequate fixation when implanted within the body. Early designs of implantable articles relied upon the use of cements such as polymethylmethacrylate to anchor the implant. The use of such cements can have some advantages, such as providing an immediate and secure fixation that does not develop free play. However, the current trend is to use these cements to a lesser extent because of their tendency to lose adhesive properties over time and the possibility that the cements will contribute to wear debris within a joint.

Recently, implantable bone prostheses have been designed such that they encourage the growth of hard tissue (i.e., bone) around the implant. Bone attachment usually occurs, and bone growth is promoted, where the surface of an implantable bone prosthesis i irregular, textured, and/or porous. The interaction of newly formed hard tissue in and around the porous textured surface of the implantable bone prosthesis has been found to provide good fixation of the prosthesis within the body. A greater degree of bone fixation can usually be achieved where bone engaging surfaces of an implantable bone prosthesis are more porous or irregular.

Porous or irregular surfaces can be provided in implantable articles by a variety of techniques. In some instances an irregular surface pattern or surface porosity is formed in an implantable bone prosthesis by post-casting techniques such as embossing, chemical etching, milling or machining. One drawback to using such techniques to provide irregular bone in-growth surfaces in implantable bone prostheses is the significant amount of post-processing time required. Such post-processing operations lead to delays in obtaining the finished product and also significantly increase the cost of manufacturing the device. These post-processing operations can also diminish the mechanical properties of the device.

Textured surfaces are also applied to implantable bone prostheses by joining a plurality of beads to an exterior surface of the prosthesis to provide separate porous surfaces or pore-forming surfaces. Beads can be joined to or formed on implantable bone prostheses by sintering small metal particles or powders to surfaces of the prostheses in desired patterns. Wire-based pads or grids can also be fused to implantable bone prostheses to provide a texture or surface relief features. A drawback of such techniques is that the sintering step required to fuse such materials to bone prostheses is a high-temperature post-processing step that can impart mechanical weaknesses to the prosthesis, distort the dimensions of the prosthesis, and/or alter the properties of the materials from which the prosthesis is made.

Accordingly, there is a need for implantable prostheses with porous surface regions that enhance the fixation mechanics of the implantable prostheses to hard tissue within the body and maintain the mechanical properties of the prostheses. There is also a need for improved methods of forming prostheses with porous surface regions.

It is thus an object of the invention to provide improved techniques for manufacturing bone prostheses having porous surfaces while preserving the mechanical properties of the prostheses. A further object is to provide methods of achieving porous surface regions in cast bone prostheses during casting operations. Another object is to provide bone prostheses having improved fixation mechanics. These and other objects will be apparent from the description that follows.

SUMMARY OF THE INVENTION

These and other objects are achieved in an implantable prosthesis having porous surface regions that are formed separately and applied to the prosthesis during the casting process, and the methods for forming such a prosthesis. The implantable prosthesis of the invention contains one or more metallic porous textured bead preforms that are applied during the casting process to a metallic prosthesis component. The bead preforms, which contribute a surface texture and a porosity to the prosthesis, are present within the casting mold and are securely attached to the resulting cast articles.

Implantable bone prostheses having porous surfaces can be manufactured according to a casting process as follows. Metallic bead preforms, which provide the desired surface texture and porosity, are first formed. These bead preforms can be made by forming a slurry of beads (e.g., metallic beads) and binder; placing the bead/binder slurry into a substrate such as a mold or form; and firing the bead/binder/mold composite to burn off binder and to sinter the beads to one another. The mold or form preferably is an inert substrate that does not bind to the beads at the sintering temperature. The mold or form should be in the shape ultimately desired for the bead preform.

The resulting bead preforms are applied, in desired regions, to one or more solid, heat disposable patterns of a prosthesis to be cast. A plurality of patterns so prepared can be assembled to a central riser system, such as a wax tree, to form a cluster. Thereafter, a shell is built around the individual patterns or the entire cluster in one or more layers by spraying or dipping in a refractory material to form an investment assembly.

Heat is typically applied to remove the solid patterns from the investment assembly, leaving behind a shell within which the bead preforms remain attached. After removal of the solid patterns, the shell can be fired to add strength and to remove any residue resulting from the solid patterns. The shell is then filled with a molten casting material. After cooling, solid cast articles are formed in which the porous bead preforms are securely embedded. Finally, the shell is removed from the solid cast articles by chemical and/or mechanical methods.

DETAILED DESCRIPTION OF THE INVENTION

Figure 1A:
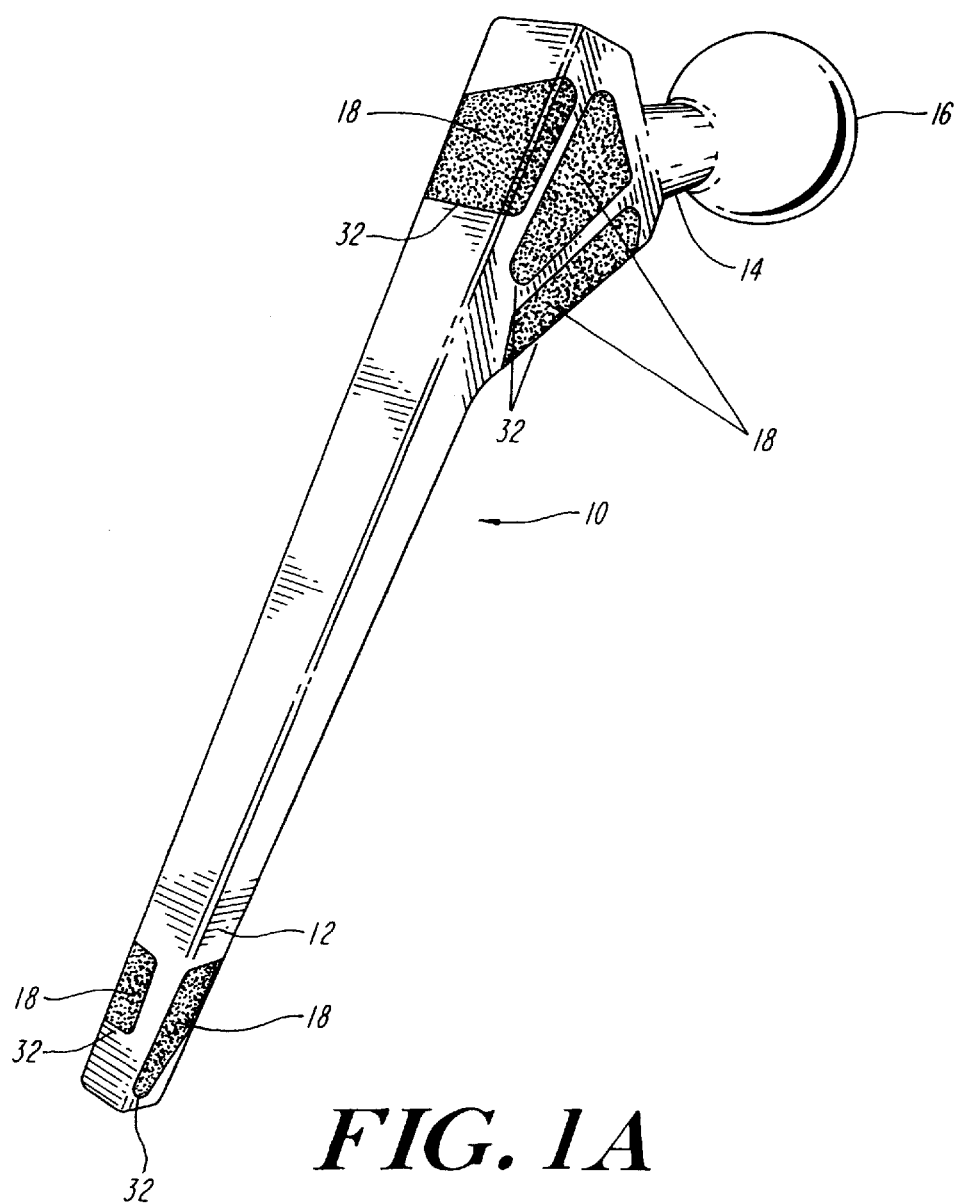
FIG. 1A is a side perspective view of a femoral stem for a human hip prosthesis formed according to the present invention, having metallic bead preforms secured thereto during casting to form a porous surface in selected regions thereof.
Figure 1B:
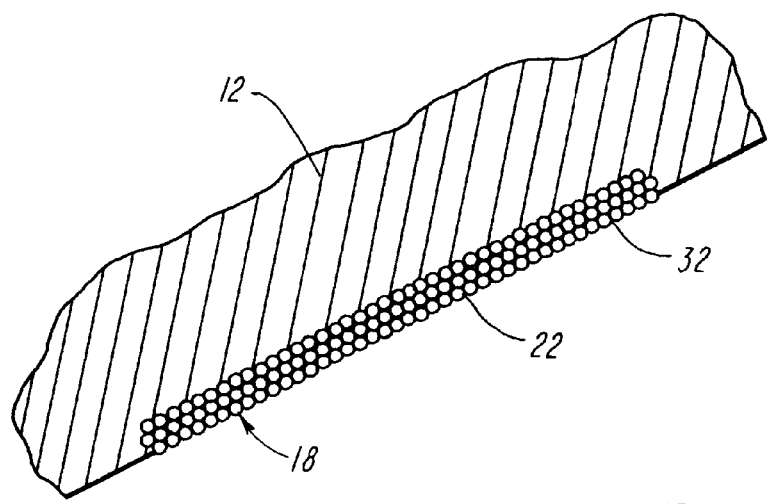
FIG. 1B is a detail view of a porous region of the prosthesis shown in FIG. 1A.

The present invention enables the production of implantable bone prostheses having beaded porous surface regions. As shown in Figs. 1A and 1B, implantable bone prosthesis 10, which by way of example is a femoral hip stem, includes a stem region 12, neck region 14 and a head 16. Stem region 12 includes bead preforms 18 which form porous, textured surface regions 32 at selected regions of the prosthesis 10. FIG. 1B illustrates a detail view of a porous, textured surface region 32 in which a plurality of indentations are formed.

Figure 2:
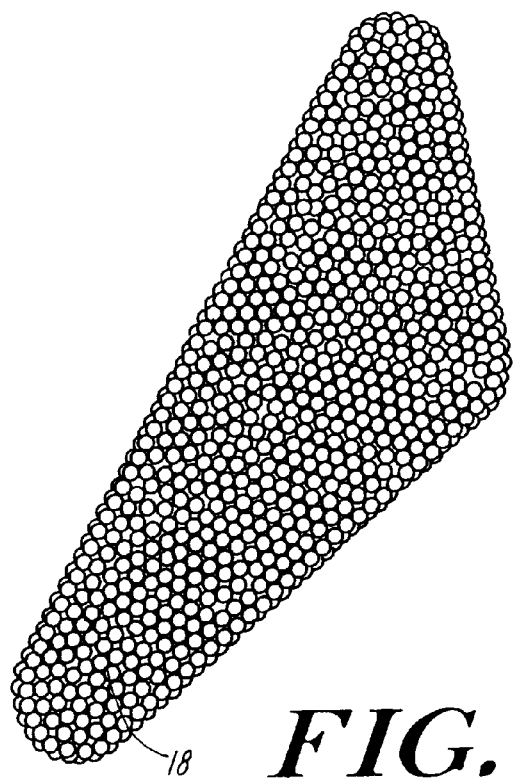
FIG. 2 is a top view of a bead preform useful with the present invention.

FIG. 2 illustrates an exemplary bead preform 18 that may be used in connection with the present invention. Bead preform 18 includes a plurality of small beads 22, or similar particles, which are joined together in multiple layers, to form the substantially porous preform.

Bead preforms can be formed by initially mixing beads (e.g., metallic beads) and binder to form a viscous bead/binder slurry. The bead/binder slurry is then applied to a non-reactive substrate which, in one embodiment, is formed to a shape that corresponds to the shape of a selected region of the prosthesis 10 where the bead preform 18 ultimately is to be located. The bead/binder slurry is allowed to solidify. Additional layers of the bead/binder slurry can then be added to the substrate to form the more complicated geometries required for some implantable articles. Other implantable articles with more simple geometries normally require only one application of the bead/binder slurry to the substrate. Once the desired number of bead/binder slurry layers have been applied to the substrate and have solidified, the bead/binder/substrate composite is fired at a temperature sufficient to burn out the binder and to sinter the beads to each other. The firing can be conducted at temperature ranges which will be apparent to those of ordinary skill in the art in a single or multi-stage process. A preferred temperature range is about 1000 to 1400° C.

The firing is preferably conducted under a protective atmosphere to avoid oxidation of the metal beads. A protective atmosphere includes an inert atmosphere, a vacuum atmosphere, a blanket of inert gases which displace ambient air, or other similar protective environments well known in the art. After the sintering, a bead preform 18 is obtained and is suitable for use in connection with the invention.

A variety of known biocompatible metals or metals having high strength and durability can be used to form the bead preforms. Exemplary materials include stainless steel, titanium, titanium alloys and cobalt-chromium alloys, and other materials that are well known for use in the manufacture of implantable bone prostheses. A particularly preferred metal alloy includes ASTM F-75.

The beads which are used to make the bead preforms of the present invention can be of a variety of different sizes. One of ordinary skill in the art will be able to determine the proper sizes for the beads based on the type and application of the implantable prosthesis being formed. Generally, the beads can have a nominal diameter of about 0.01 to about 0.035 inch. Preferably, the beads can have a diameter of about 0.02 to about 0.022 inch.

The beads used to prepare the preform preferably have a narrow particle size distribution. Alternatively, the particle size distribution can be bimodal.

A variety of binder materials that have solidifying properties at room temperature can be used to form the bead/binder slurry. Exemplary binder solvents include cellulosic materials, such as methyl cellulose, and other materials that are well known for use as binders, and which dry and harden at room temperature.

One of ordinary skill in the art will be able to determine the proper concentration of the beads in the bead/binder slurry based upon the type and application of the implantable prosthesis being formed. Generally, a preferred concentration of beads in the bead/binder slurry ranges from about 50% to about 75% by volume.

The thickness of the resulting bead preform can vary depending upon the requirements of a given application. The bead preforms typically are about 2 to 4 bead layers in thickness. In a preferred embodiment, the thickness of the bead preforms ranges from about 0.015 to about 0.70 inches.

The invention enables an investment casting process to be used to obtain implantable articles, such as bone prostheses, that include porous beaded regions. Although the invention is described with respect to an implantable hip femoral component, it is understood that the invention is applicable to the manufacture of other joint prostheses and implantable articles as well.

Figure 3:
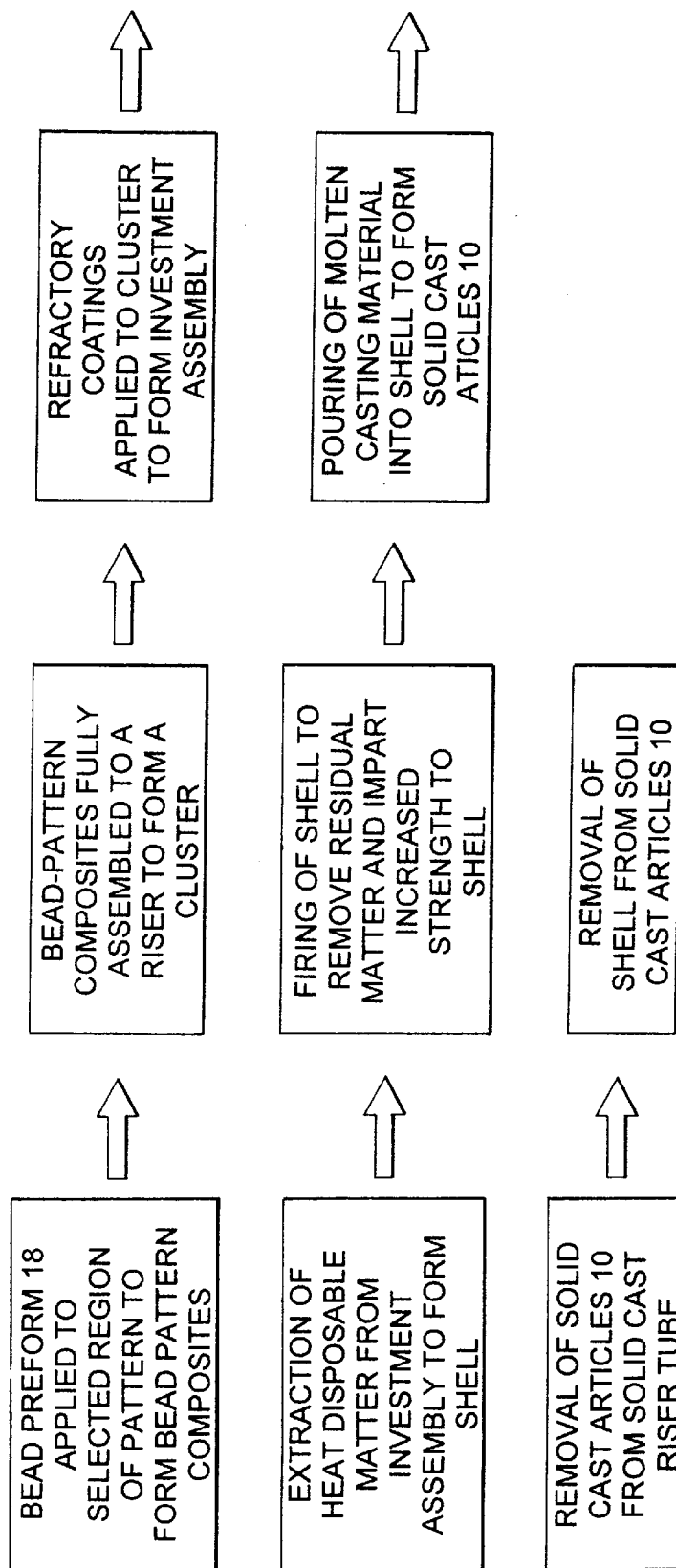
FIG. 3 is a flow chart showing successive stages in the casting process in accordance with the features of the invention.

FIG. 3 is a flow chart showing the successive stages in the casting process in accordance with the features of the invention. A bead preform 18 is applied to a selected region of a solid, heat disposable pattern of an implantable article. This step can be accomplished by heating the bead preform 18 to a temperature sufficient to soften or to cause some melting of the pattern once it contacts the pattern. A preferred temperature range is from about 70° C. to about 90° C. The preform 18 is then pressed onto the pattern to the extent that approximately 25% of the preform is disposed within the pattern, in a desired location thereof. Upon cooling, the preform remains affixed to the pattern.

The application of bead preform 18 to the pattern forms a bead-pattern composite. One or more bead-pattern composites can then be joined to a riser, as is known in the art, to form a cluster.

One or more coatings of a refractory can then be applied to the cluster of bead-pattern composites by a number of known techniques, such as by spraying or dipping. The refractory preferably is applied in layers that filly coat the exterior surfaces of the cluster, with drying cycles provided between each application of refractory. As understood by those having ordinary skill in the art, primary layers are typically applied before the application of one or more backup layers of refractory. Primary coats of refractory tend to be finer as they must accurately adhere to the contours of the bead-pattern composites. Backup coats of refractory tend to be more coarse as they are primarily intended to impart structural strength. The resulting refractory-coated cluster forms an investment assembly.

After forming the investment assembly the heat disposable matter which forms the solid patterns and the riser tube can be extracted by a number of known techniques. For example, the heat disposable matter can be extracted by placing the investment assembly in a heated, pressurizable chamber or oven. According to known techniques, heat and/or pressure are applied to such a degree that the heat disposable matter vaporizes, or melts and flows out of the investment assembly.

Following extraction of the heat disposable matter from the investment assembly, a ceramic shell is obtained. The ceramic shell includes cavities formerly occupied by the heat disposable patterns, which form the negative image of the desired articles to be cast. Further, the bead preforms 18 remain attached to the interior portion of the shell cavities.

Shell 56 can then be heated and fired, to impart increased strength to the shell and to remove any residual heat disposable matter. In a preferred embodiment, the firing should be conducted under a protective atmosphere to avoid oxidation of the metal beads. Preferably, this step is conducted at about 800° F. to about 2000° F. for about 15 to about 60 minutes, or more. The shell is then ready to accept molten casting material. The casting material is poured into and fills the shell and its cavities to form solid cast articles. Once the cavities are filled, the molten metal is allowed to cool (optionally in a protective atmosphere) and to solidify. Thereafter, the refractory shell is fractured or otherwise removed, leaving behind the desired solid, cast articles 10 attached to a solid cast riser tube. The cast articles 10 can be removed from the solid cast riser tube by known mechanical methods. As noted above, the resulting cast article includes one or more bead preforms securely embedded therein.

The use of solid, heat disposable patterns and various types of riser tubes is also well known in the art of investment casting. Suitable materials that can be used to form heat disposable patterns are those that are solid at room temperature and melt at elevated temperatures (e.g., about 150° F. and higher). Another requirement of materials used to form the solid, heat disposable patterns is that they be sufficiently meltable upon exposure to a preheated bead preform such that the bead preform will remain adhered within the pattern. Exemplary materials are known casting waxes, photocurable polymers, and moldable thermoplastics. Exemplary moldable thermoplastics include polystyrenes, nylons and polyolefins.

Riser tubes can be made out of similar heat disposable materials. Alternatively, the riser tube can be a hollow tube made from a non-heat disposable material, such as ceramic.

A variety of refractory materials well known for use in investment casting processes can be used with the process of the present invention. Examples of suitable refractory materials include those that utilize colloidal silica binder, alcohol based binder, latex binder additive, and colloidal silica binder with a latex additive. A preferred primary refractory is a fine stucco with a high percentage of zircon. Preferred backup coats are generally more coarse than the primary coat and typically use colloidal silica binder with fused silica.

The present invention is applicable to the manufacture of virtually any article that can be cast. It is understood that the bead preforms made and used according to the present invention, and the components thereof, may have shapes and sizes other than those recited in this exemplary description.

The foregoing description of methods of manufacture and the illustrative embodiment is presented to indicate the range of constructions to which the invention applies. Variations in the casting process of the invention and the materials to be used in the casting process of the invention will be readily apparent to those having ordinary skill in the art. Such variations are considered to be within the scope of the invention in which patent rights are asserted, as set forth in the claims appended hereto.

What is claimed is:

1. A method of forming an implantable prosthesis comprising the steps of:
   (a) forming a bead preform, wherein the bead preform has a first and a second porous textured surface;
   (b) embedding the first porous textured surface of the bead preform into a non-metallic solid heat disposable pattern of an article to form a bead-pattern composite;
   (c) applying at least one coating of a refractory to the porous textured second surface of the composite to form an investment assembly, thereby forming a shell;
   (d) removing the non-metallic solid heat disposable pattern from the investment assembly, thereby providing a formed shell with the second surface of the bead preform embedded therein and having the first porous textured surface exposed therefrom;
   (e) filling the formed shell with a molten casting material such that the molten casting material fills the shell to form, upon cooling, a cast article; and
   (f) removing the formed shell from the cast article to yield the cast article having the bead preform embedded within the cast article, wherein the embedded bead preform has the porous textured second surface exposed.

2. The method of claim 1, further including the step of joining multiple bead-pattern composites to a riser system to yield a cluster.

3. The method of claim 2, further including performing steps of (c) through (f) on the cluster.

4. The method of claim 1, wherein the step of forming the bead preform comprises the steps of
   forming a slurry of a plurality of beads and a binder;
   applying the bead/binder slurry to a dimensionally stable substrate and allowing the bead/binder slurry to solidify to form a bead/binder/substrate composite; and
   firing the bead/binder/substrate composite to burn off the binder and to sinter the beads to one another, yielding a bead preform.

5. The method of claim 4, wherein the beads are formed of a metal or a metal alloy and have a nominal diameter in the range of about 0.01 to about 0.035 inches.

6. The method of claim 4, wherein the binder is formed of a cellulosic-based material.

7. The method of claim 4, wherein a concentration of beads in the bead/binder slurry is about 50% to about 75% by volume.

8. The method of claim 4, wherein the substrate is formed of a non-reactive ceramic.

9. The method of claim 4, wherein the firing step is conducted in a protective atmosphere at a temperature in the range of about 1000° C. to about 1400° C.

10. The method of claim 1, wherein the step of applying the bead preform to the solid disposable pattern comprises the step of preheating the bead preform and pressing the preheated preform into the solid pattern in a desired location thereof.

11. The method of claim 10, wherein the bead preform is preheated to approximately 70–90° C. before application to the solid pattern.

12. The method of claim 10, wherein the step of preheating the bead preform and pressing the preheated preform into the solid pattern comprises preheating and imbedding the bead preform within the solid pattern to the extent that approximately 25% of the surface area of a bead perform is disposed within the solid pattern.

13. The method of claim 1, wherein the step of forming the shell around the bead-pattern composite comprises dipping the bead-pattern composite in one or more slurries of the refractory material, or spraying the slurries on the bead-pattern composite.

14. The method of claim 1, wherein the step of removing the solid pattern from the investment assembly comprises heating the solid pattern to melt and/or destroy the non-metallic solid heat disposable pattern.

15. The method of claim 1, further comprising the step of:
preheating the investment assembly prior to filling the shell with molten casting material under a protective atmosphere.

16. The method of claim 1, wherein the step of filling the shell with a molten casting material comprises filling the shell with a molten metallic casting material under a protective atmosphere.

* * * * *